United States Patent [19]

Marsili et al.

[11] Patent Number: 4,590,185
[45] Date of Patent: May 20, 1986

[54] 3-AZINOMETHYL RIFAMYCINS

[75] Inventors: Leonardo Marsili; Marco Falciani; Renato Broggi, all of Milan, Italy

[73] Assignee: DOBFAR S.p.A., Milan, Italy

[21] Appl. No.: 718,085

[22] Filed: Apr. 1, 1985

[30] Foreign Application Priority Data

Apr. 6, 1984 [GB] United Kingdom ............... 8408924

[51] Int. Cl.[4] ................. A61K 31/395; C07D 498/08
[52] U.S. Cl. ............................. 514/183; 260/239.3 P; 514/321; 514/422; 514/255
[58] Field of Search ............. 260/239.3 P; 514/183, 514/321, 422, 255

[56] References Cited

U.S. PATENT DOCUMENTS 4,447,432  5/1984  Franceschi et al. .......... 260/239.3 P Primary Examiner—Robert T. Bond
Attorney, Agent, or Firm—Oblon, Fisher, Spivak, McClelland & Maier

[57] ABSTRACT

There are provided 3-azinomethyl rifamycins of the formula I:

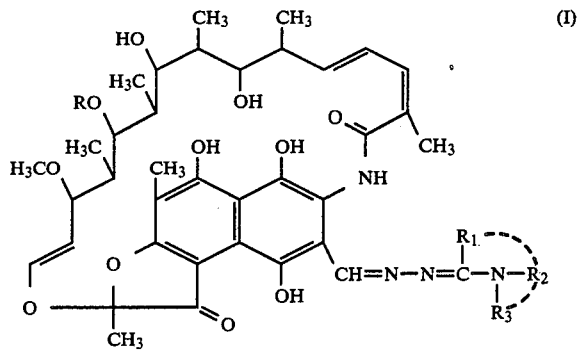

wherein
R represents hydrogen or acetyl;
$R_1$ represents hydrogen or lower alkyl;
$R_2$ represents an alkyl group having from 2 to 4 carbon atoms substituted by a dialkoxy group each having from 1 to 3 carbon atoms;
$R_3$ represents an alkyl group having from 1 to 4 carbon atoms;
$R_2$ and $R_3$ may form with the amino nitrogen atom a 4- to 8-membered heterocyclic ring, having a maximum of two hetero atoms, substituted by hydroxy-, alkoxy-, dialkoxy- or alkylenedioxy groups each having from 1 to 4 carbon atoms, arylalkoxyimino groups having from 7 to 9 carbon atoms, acyloxy groups having from 1 to 4 carbon atoms;
$R_1$ and $R_2$ may form with the amino nitrogen atom and the carbon atom a 5 to 7-membered heterocyclic ring optionally substituted by alkyl or alkoxy group having from 1 to 4 carbon atoms.

The compounds display antibacteria activity against Gram-positive and Gram-negative bacteria and Mycobacteria. Process for the preparation of the above compounds and their pharmaceutical compositions are also described and claimed.

10 Claims, No Drawings

3-AZINOMETHYL RIFAMYCINS

The invention provides 3-azinomethyl rifamycins, having the general formula I:

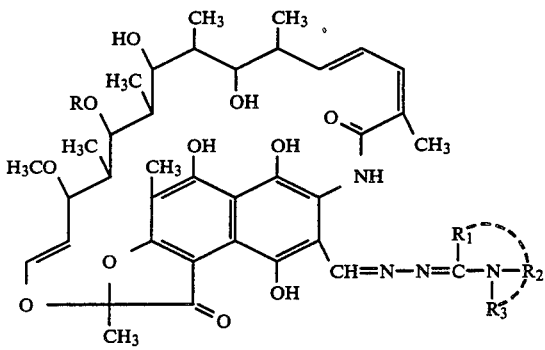

wherein
R represents hydrogen or acetyl:
$R_1$ represents hydrogen or lower alkyl;
$R_2$ represents an alkyl group having from 2 to 4 carbon atoms substituted by a dialkoxy group each having from 1 to 3 carbon atoms;
$R_3$ represents an alkyl group having from 1 to 4 carbon atoms;
$R_2$ and $R_3$ may form with the amino nitrogen atom a 4- to 8-membered heterocyclic ring, having a maximum of two hetero atoms, substituted by hydroxy-, alkoxy-, dialkoxy- or alkylenedioxy groups each having from 1 to 4 carbon atoms, arylalkoxyimino groups having from 7 to 9 carbon atoms, acyloxy groups having from 1 to 4 carbon atoms;
$R_1$ and $R_2$ may form with the amino nitrogen atom and the carbon atom a 5- to 7-membered heterocyclic ring optionally substituted by alkyl or alkoxy group having from 1 to 4 carbon atoms.

The class of rifamycins encompass a large number of compounds which have shown to be very interesting for their antibacterial activity. Products of this class, but differing from those of the present invention in the side chain of the 3-position, are disclosed in the U.S. Pat. Nos. 4,124,585, 4,124,586, 4,164,499, 4,165,317, 4,175,077, 4,217,278 and 4,447,432.

The present invention also provides processes for the manufacture of the above characterized compounds of the formula I.

The compounds of the formula I can be produced in a manner known "per se" by reacting 3-formyl rifamycin SV with hydrazine and with a compound of formula II:

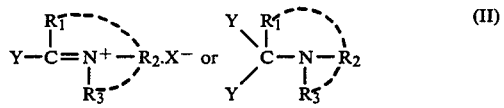

wherein Y represents an alkoxy groups, $R_1$, $R_2$ and $R_3$ have the meaning given initially and X represents an acid residue suitable to form a quaternarium salt with amino nitrogen atom.

The reaction is carried out in an inert solvent such as tetrahydrofuran, chloroform, dichloromethane.

The compounds thus obtained can be separated from the reaction mixture by crystallization according to the known procedures.

The starting material 3-formyl-rifamycins are known compounds, disclosed in U.S. Pat. No. 3,342,810. The compounds of formula II are also known or can easily prepared by conventional processes. The compounds of formula I of the rifamycin SV series can be optionally transformed into the corresponding 1,4-quinone form of the rifamycin S series by oxidation, in known manner, with an oxidizing agent such as ammonium persulphate, potassium ferricyanide or manganese dioxide. The novel compounds according to the invention have antibiotic, especially antibacteria activity, against Gram-positive and Gram-negative bacteria and against Mycobacteria and, particularly, Mycobacterium tuberculosis.

The in vitro activities of the rifamycin compounds of the present invention have been tested against some Gram-positive and Gram-negative microorganisms and against Mycobacterium Tuberculosis (serial dilution method). The results are reported in table 1, wherein the novel compounds are compared with Rifampicin and the figures are the MICs given in mcg/ml.

TABLE 1

| Microorganisms | Compounds of Examples | | | | | | Rifampicin |
| | 1 | 5 | 6 | 3 | 2 | 4 | |
| --- | --- | --- | --- | --- | --- | --- | --- |
| S. aureus ATCC6538P | 0.1 | 0.1 | 0.1 | 0.1 | 0.1 | 1 | 0.1 |
| S. epidermidis BB0223 | 0.1 | 0.1 | 0.1 | 0.1 | 1 | 0.1 | 0.1 |
| S. lutea ATCC9341 | 0.1 | 0.1 | 0.1 | 0.1 | 0.1 | 0.1 | 0.1 |
| B. subtilis ATCC6633 | 1 | 1 | 1 | 0.1 | 1 | 1 | 0.1 |
| K. pneumoniae ATCC10031 | 1 | 0.1 | 100 | 10 | 100 | 100 | 1 |
| Mycobacterium Tub. H37RV | 10 | 1 | 1 | 1 | 1 | 10 | 0.1 |

The invention relates also to pharmaceutical preparations containing one of the above compounds of formula I together with a pharmaceutical suitable carrier or diluent.

The following examples illustrate the present invention without limiting its scope.

EXAMPLE 1

3-(1-methyl-pyrrolidin-2-ylidenyl-azinomethyl)rifamycin SV 6 g of 1-methyl-2-methoxy-$\Delta^1$-pyrrolinium-methyl sulphate [Chem.Berichte 97, 3076, (1964)] were reacted with 2,5 g of 80% hydrazine hydrate and the resulting crude product was added to a solution of 3,6 g of 3-formyl-rifamycin SV in 60 ml of tetrahydrofuran.

After stirring for 15 minutes at 30° the reaction mixture was diluted with 250 ml of methylene chloride, washed with water acidified to pH3 with diluted hydrogen chloride and then with water several times. After drying on anhydrous sodium sulphate, the solvent was evaporated off in vacuo and the residue was crystallized from ethyl alcohol. 2.2 g of a red compound were obtained having formula I wherein: R is —COCH$_3$ and

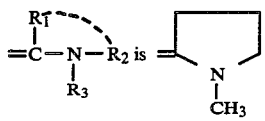

Rf=0.49 in CHCl$_3$/MeOH (9:1)

PMR(CDCl$_3$):−0.27 δ[d,CH$_3$(34)]; 0.71 δ[d, CH$_3$(33)]; 0.75 δ[d,CH$_3$(31)]; 0.98 δ[d, CH$_3$(32)]; 1.78 δ[s, CH$_3$(13)]; 2.06 δ[s, CH$_3$(36)]; 2.10 δ[s, CH$_3$(30)]; 2.22 δ[s, CH$_3$(14)]; 2.93 δ[s, N CH$_3$]; 3.04 δ[s, CH$_3$(37)]; 4.92 δ[d, H(25)]; 5.10 δ[dd, H(28)]; 5.84 δ[ddd, H(19)]; 6.2–6.4 δ[m, H(17), H(18), H(29)]; 9.04 δ[s, CH=N—N=]; 11.94 δ[s, OH—C(4)]; 13.17 δ[s,—N—H—CO—]; 13.32 and 13.42 δ[s, OH—C(1), OH—C(8)].
MS: 820(M+).

EXAMPLE 2

3-(1-methyl-piperidin-2-ylidenyl-azinomethyl)rifamycin SV 6.5 g of 1-methyl-2-methoxy-δ$^1$-tetrahydro-pyridinium-methyl sulphate was reacted with 2 g of hydrazine hydrate and the crude hydrazono derivative was added to a solution of 2.4 g of 3-formyl-rifamycin SV in 40 ml of tetrahydrofuran. The reaction mixture was stirred for 24 h, then was diluted with 200 ml of methylene chloride and washed with water. After drying on anhydrous sodium sulphate, the solvent was evaporated off in vacuo and the residue was crystallized from methylene chloride/isopropyl ether.

1.5 g of a compound of formula I was obtained wherein R is COCH$_3$ and

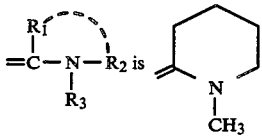

Rf=0.37 in CHCl$_3$/MeOH (9:1).
MS: 834 (M+).

EXAMPLE 3

3-(1-ethyl-pyrrolidin-2-ylidenyl-azinomethyl)rifamycin SV 6.5 g of 1-ethyl-2-methoxy-Δ$^1$-pyrrolinium-methyl sulphate was reacted with 2 g of hydrazine hydrate and the resulting crude product was added to a solution of 3.6 g of 3-formyl rifamycin SV in 60 ml of tetrahydrofuran. The mixture was stirred for 30 minutes at room temperature, then was diluted with 200 ml of methylene chloride and washed with water. After drying on anhydrous sodium sulphate, the solution was concentrated to 60 ml and allowed to crystallize.

2.1 g of a red compound was obtained having formula I wherein R is COCH$_3$ and

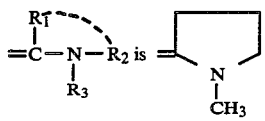

Rf=0.47 in CHCl$_3$/MeOH (9:1).
MS: 834 (M+).

EXAMPLE 4

3-(4'-hydroxy-piperidinomethylene-azinomethyl)rifamycin SV 4 g of 3-formyl-rifamycin SV was dissolved in 75 ml of Tetrahydrofuran containing 0.5 ml of hydrazine hydrate.

5 g of N-formyl-4-hydroxy-piperidine dimethylacetal was added to the solution and allowed to react under stirring for 24 h. The reaction mixture was diluted with methylene chloride (200 ml) and washed with water. After drying on anhydrous sodium sulphate the solvent was evaporated off in vacuo. The residue was crystallized from methanol. 1.9 g of a red compound of general formula I, wherein R is COCH$_3$, R$_1$ is H and NR$_2$R$_3$ is

Rf=0.38 in CHCl$_3$/MeOH (9:1).
MS=850 (M+).

EXAMPLE 5

3-[(8-aza-1,4-dioxa-spiro[4,5]dec-8-yl)-methylene-azinomethyl]rifamycin SV 7 g of 3-formyl-rifamycin SV were added to a solution of 0.9 ml of 80% hydrazine hydrate in 75 ml of tetrahydrofuran at 0° C. 5 ml of N-formyl-4-piperidone-ethylene-ketal dimethylacetal were dropped to the resulting mixture and warmed to 35° C. for 2 hours. After dilution with 200 ml of methylene chloride, the solution was washed with water acidified to pH3 and then with water several times. After drying on anhydrous sodium sulphate, the solvent was evaporated off in vacuo and the product was crystallized from ethyl acetate. 3.5 g of a compound were obtained, having the formula I wherein R is —COCH$_3$, R$_1$ is H and

is 4-ethylene-dioxy-piperidyl group
Rf=0.67 in CHCl$_3$/MeOH (9:1)
PMR (CDCl$_3$): −0.31 δ[d,CH$_3$(34)]; 0.64 δ[d, CH$_3$(33)]; 0.74 δ[d, CH$_3$(31)]; 0.98 δ[d, CH$_3$(32)]; 1.78 δ[s, CH$_3$(13)]; 2.05 δ[s, CH$_3$(36)]; 2.10 δ[s, CH$_3$(30)]; 2.21 δ[s, CH$_3$(14)]; 3.02 δ[s, CH$_3$(37)]; 3.99 δ[s, OCH$_2$—CH$_2$O]; 4.90 δ[d, H(25)]; 5.08 δ[dd, H(28)]; 5.86 δ[ddd, H(19)]; 6.26 δ[d, H(29)]; 6.35 δ[dd, H(17)]; 6.57 δ[dd, H(18)]; 7.73 δ[s, CH=N—N=CH—N]; 9.00 δ[s, CH=N—N=CH—N]; 11.95 δ[s, OH—C(4)]; 13.25 δ[bs, OH—C(1), OH—C(8)]; 13.77 δ[s,—NH—CO—].
MS: 892 (M+).

EXAMPLE 6

3-(N-methyl-β-dimethoxyethylaminomethylene-azinomethyl)rifamycin SV 0.4 ml of hydrazine hydrate was added to a mixture of 5.4 g of 3-formylrifamycin SV and 90 ml of tetrahydrofuran at room temperature. After ten minutes stirring, 5 ml of N-methyl-N-β-dimethoxyethylformamide dimethylacetal was dropped into the resulting solution of 3-hydrazonomethyl-rifamycin SV and the mixture was allowed to react at 25° C. for 30 minutes. 300 ml of dichloromethane was added and the organic solution was washed with water.

After drying on anhydrous sodium sulphate the solvent was evaporated off and the residue was crystallized from methanol. 3.9 g of a compound of general formula I wherein R is $COCH_3$, $R_1$ is H, $R_2$ is $CH_3$ and $R_3$ is $CH_2CH(OCH_3)_2$.

Rf: 0.67 in $CHCl_3$:MeOH 9:1.
MS: 868 (M+).

EXAMPLE 7

3-(4-formyl-piperazino methylene-azinomethyl)-rifamycin SV 1.8 g of 3-formyl-rifamycin SV were reacted with 0.125 ml of hydrazine hydrate in 30 ml of tetrahydrofuran at room temperature for 15 minutes. The reaction mixture was added with 8 g of N-formylpiperazine-dimethyl acetal and allowed to stand at 35° C. for 60 minutes. After diluting with 200 ml of methylene dichloride and washing with water several times, the solvent was evaporated off and the product was crystallized from ethyl acetate. 0.80 g of a compound were obtained having formula I wherein R is —$COCH_3$, $R_1$ is H and

is 4-formyl-piperazinyl group
Rf=0.42 in $CHCl_3$/MeOH (9:1)
PMR($CDCl_3$): —0.29 δ[d, $CH_3$(34)]; 0.64 δ[d, $CH_3$(33)]; 0.73 δ[d, $CH_3$(31)]; 0.99 δ[d, $CH_3$(32)]; 1.79 δ[s, $CH_3$(13)]; 2.06 δ[s, $CH_3$(36)], 2.10 δ[s, $CH_3$(30)]; 2,23 δ[s, $CH_3$(14)]; 3.03 δ[s, $CH_3$(37)]; 4.92 δ[d, H(25)]; 5.11 δ[dd, H(28)]; 5.86 δ[ddd, H(19)]; 6.25 δ[d, H(29)]; 6.36 δ[dd, H(17)]6.57 δ[dd, H(18)]; 7.78 δ[s, CH=N—N=CH—N]; 8.12 δ[s, CHO]; 9.05 δ[s, CH=N—N=CH—N]; 12.04 δ[s, OH—C(4)]; 13.27 δ[bs, OH—C(1), OH—C(8)]; 13.59 δ[s, —NH—CO—].
MS: 863 (M+).

EXAMPLE 8

3-(4-benzyloxyimino-piperidinomethylene-azinomethyl rifamycin SV 3.6 g of 3-formyl-rifamycin SV were added to a solution of 0.25 ml of hydrazine hydrate in 50 ml of tetrahydrofuran at 0° C. After stirring for 10 minutes 3.5 g of N-formyl-4-benzyloxy-imino-piperidine-dimethyl acetal were added. The reaction mixture was warmed at 40° C. for 30 minutes, diluted with 200 ml of methyl-isobutylketone, washed several times with buffered solution to a pH of 8.5 and then with water.

After evaporating the solvent in vacuo, the residue was taken up with isopropyl ether and precipitated by dilution with hexane. 1.2 g of a compound are obtained, having formula I wherein R is $COCH_3$, $R_1$ is H and

is 4-benzyloxyimino-piperidinyl group.
Rf: 0.67 in $CHCl_3$:MeOH (9:1).
MS: 953 (M+).

We claim:

1. 3-azinomethyl rifamycin having the formula (I):

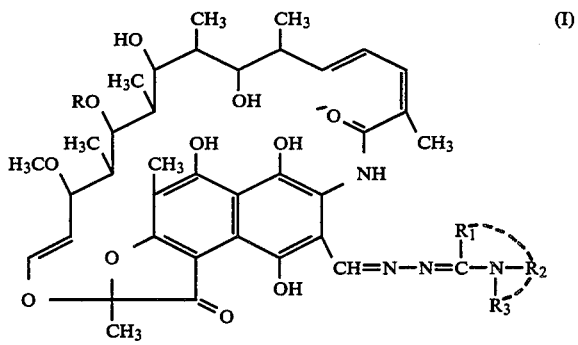

wherein
R represents hydrogen or acetyl;
$R_1$ represents hydrogen or lower alkyl;
$R_2$ represents an alkyl group having from 2 to 4 carbon atoms substituted by a dialkoxy group each having from 1 to 3 carbon atoms;
$R_3$ represents an alkyl group having from 1 to 4 carbon atoms;
$R_2$ and $R_3$ may form with the amino nitrogen atom a 4- to 8-membered saturated heterocyclic ring, having a maximum of two nitrogen atoms, wherein when there are two nitrogen atoms in said heterocyclic ring, there are no nitrogen-nitrogen bonds in said heterocyclic ring, and further wherein said heterocyclic ring is substituted by hydroxy-, alkoxy-, dialkoxy- or alkylenedioxy groups each having from 1 to 4 carbon atoms, arylalkoxyimino groups having from 7 to 9 carbon atoms, acyloxy groups of carboxylic acids having from 1 to 4 carbon atoms;
$R_1$ and $R_2$ may form with the amino nitrogen atom and the carbon atom a 5 to 7-membered saturated heterocyclic ring, said amino nitrogen being the only hetero atom, optionally substituted by alkyl or alkoxy group having from 1 to 4 carbon atoms.

2. 3-(1-methyl-pyrrolydin-2-ylidenyl-azinomethyl)-rifamycin SV.

3. 3-(1-ethyl-pyrrolydin-2-ylidenyl-azinomethyl)rifamycin SV.

4. 3-(1-methyl-piperidin-2-ylidenyl-azinomethyl)rifamycin SV.

5. 3-[(8-aza-1,4-dioxa-spiro[4,5]-dec-8-yl)-methylene-azinomethyl]-rifamycin SV.

6. 3-(4-formyl-piperazino-methylene-azinomethyl)-rifamycin SV.

7. 3-(4-benzyloxyimino-piperidino-methylene-azinomethyl)-rifamycin SV.

8. 3-(N-methyl-β-dimethoxyethyl-azinomethyl)-rifamycin SV.

9. 3-(4-hydroxy-piperidino-methylene-azinomethyl)-rifamycin SV.

10. An antibiotic composition which comprises a 3-azinomethyl-rifamycin as claimed in claim 1 in an amount sufficient to exert antibacterial activity and a pharmaceutically acceptable carrier or diluent thereof.

* * * * *